(12) United States Patent
Mastroianni et al.

(10) Patent No.: US 9,309,189 B2
(45) Date of Patent: Apr. 12, 2016

(54) METHOD FOR PRODUCING NITRILE COMPOUNDS FROM ETHYLENICALLY UNSATURATED COMPOUNDS

(71) Applicant: RHODIA OPERATIONS, Aubervillers (FR)

(72) Inventors: Sergio Mastroianni, Lyons (FR); Paul Pringle, Bristol (GB); Jonathan Hopewell, Wakefield (GB); Michael Garland, Wiltshire (GB)

(73) Assignee: INVISTA NORTH AMERICA S.A R.L., Wilmington, DE (US)

( * ) Notice: Subject to any disclaimer, the term of this patent is extended or adjusted under 35 U.S.C. 154(b) by 0 days.

(21) Appl. No.: 14/348,283

(22) PCT Filed: Sep. 27, 2012

(86) PCT No.: PCT/EP2012/069027
§ 371 (c)(1),
(2) Date: Mar. 28, 2014

(87) PCT Pub. No.: WO2013/045524
PCT Pub. Date: Apr. 4, 2013

(65) Prior Publication Data
US 2014/0249327 A1 Sep. 4, 2014

(30) Foreign Application Priority Data
Sep. 30, 2011 (FR) ...................................... 11 02976

(51) Int. Cl.
*C07C 253/10* (2006.01)
(52) U.S. Cl.
CPC .................................... *C07C 253/10* (2013.01)
(58) Field of Classification Search
CPC .................................................. C07C 253/10
See application file for complete search history.

(56) References Cited

U.S. PATENT DOCUMENTS

2011/0118499 A1* 5/2011 Mastroianni .................. 558/335

FOREIGN PATENT DOCUMENTS

| FR | 1599761 | A | 7/1970 |
| FR | 2926816 | A1 | 7/2009 |
| FR | 2937321 | A1 | 4/2010 |
| FR | 2941455 | A1 | 7/2010 |
| WO | 2010/145960 | A1 | 12/2010 |

OTHER PUBLICATIONS

Fey et al. "Stable Fluorophosphines: Predicted and Realized Ligands for Catalysis" Angew. Chem. Int. Ed. 2012, 51, 118-122 (Nov. 11, 2011).*
Fidal et al., "Phosphorus—Fluorine Chemistry. Part XXIII. T-Butyl-Fluorophosphines and -Fluorophosphoranes and their Derivatives", Journal of the Chemical Society A: Inorganic, Physical, Theoretical, 1970, pp. 2359-2364.
Olah, Goerge A, "Friedel-Crafts and Related Reactions", General Aspects vol. 1, 1963, pp. 191-197.
International Preliminary Report on Patentability received for PCT Patent Application No. PCT/EP2012/069027, mailed on Apr. 1, 2014, 6 pages.
International Search Report and Written Opinion received for PCT Application No. PCT/EP2012/069027, mailed on Nov. 9, 2012, 11 pages.
Weast et al., "CRC Handbook of Chemistry and Physics", Chemical Rubber Company, 1970-1971, 51st Edition.

* cited by examiner

*Primary Examiner* — Joseph Kosack
*Assistant Examiner* — Amanda L Aguirre
(74) *Attorney, Agent, or Firm* — Robert B. Furr, Jr.; Jeffrey Freeman

(57) ABSTRACT

The present invention relates to a method for the hydrocyanation of organic ethylenically unsaturated compounds including at least one nitrile function. The invention specifically relates to a method for the hydrocyanation of a hydrocarbon compound including at least one ethylenic unsaturation by a reaction with hydrogen cyanide in a liquid medium and in the presence of a catalyst including a metal element selected from the transition metals and an organophosphorous ligand, the organophosphorous ligand including a compound of general formula (I), where $R_1$ and $R_2$, which are identical or different, are a linear or branched alkyl radical having 1-12 carbon atoms, which can include heteroatoms, or an optionally substituted aromatic or cycloaliphatic radical that can include heteroatoms, wherein the covalent bond between P and $R_1$, and that between P and $R_2$, are P—C bonds.

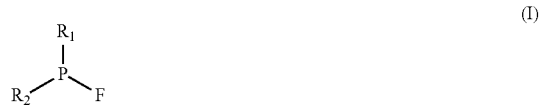

(I)

17 Claims, No Drawings

METHOD FOR PRODUCING NITRILE COMPOUNDS FROM ETHYLENICALLY UNSATURATED COMPOUNDS

RELATED APPLICATIONS

This application is a U.S. national stage entry under 35 U.S.C. §371 of International Application No. PCT/EP/2012/069027, filed Sep. 27, 2012, which claims priority to FR 1102976 filed on Sep. 30, 2011. The entire contents of these applications are explicitly incorporated herein by this reference.

The present invention relates to a process for the hydrocyanation of ethylenically unsaturated organic compounds to give compounds comprising at least one nitrile functional group.

It relates more particularly to the hydrocyanation of diolefins, such as butadiene, or of substituted olefins, such as alkenenitriles, for example pentenenitriles.

The hydrocyanation reaction is, for example, described in French patent No. 1 599 761, which relates to a process for the preparation of nitriles by addition of hydrocyanic acid to organic compounds having at least one ethylenic double bond, in the presence of a catalyst comprising nickel and an organophosphorus ligand, a friary! phosphite. This reaction can be carried out in the presence or in the absence of a solvent.

When a solvent is used, it is preferably a hydrocarbon, such as benzene or xylenes, or a nitrile, such as acetonitrile.

The catalyst employed is an organic complex of nickel comprising ligands, such as phosphines, arsines, stibines, phosphites, arsenites or antimonites.

The presence of a promoter for activating the catalyst, such as a boron compound or a metal salt, generally a Lewis acid, is also recommended in said patent.

Many other catalytic systems have been provided, generally comprising organophosphorus compounds belonging to the family of the phosphites, phosphonites, phosphinites and phosphines. These organophosphorus compounds can comprise one phosphorus atom per molecule and are described as monodentate ligands or can comprise several phosphorus atoms per molecule; they are then known as polydentate ligands. More particularly, many ligands comprising two phosphorus atoms per molecule (bidentate ligands) have been described in many patents.

However, the search for novel catalytic systems which are more effective, both in catalytic activity and in stability, is still being undertaken in order to improve the general economics of the process.

One of the aims of the present invention is to provide a novel family of ligands which makes it possible to obtain, with the transition metals, catalytic systems exhibiting a good catalytic activity, in particular in hydrocyanation reactions.

To this end, the present invention provides a process for the hydrocyanation of an organic compound comprising at least one ethylenic unsaturation by reaction, in a liquid medium, with hydrogen cyanide in the presence of a catalyst comprising a metal element chosen from transition metals and an organophosphorus ligand, the organophosphorus ligand comprising a compound corresponding to the general formula (1):

(I)

in which:
$R_1$ and $R_2$, which are identical or different, represent a linear or branched alkyl radical having from 1 to 12 carbon atoms which can comprise heteroatoms, or a radical comprising a substituted or unsubstituted aromatic or cycloaliphatic radical which can comprise heteroatoms, the covalent bond between P and $R_1$, on the one hand, and that between P and $R_2$, on the other hand, are P—C bonds.

Advantageously, $R_1$ and $R_2$ represent a linear or branched alkyl radical having from 1 to 12 carbon atoms which can comprise heteroatoms.

Mention may be made, as compound of general formula (I) suitable for the process of the invention, for example, of $^tBu_2PF$.

The compounds of general formula (I) can be prepared according to any method known to a person skilled in the art. They can, for example, be obtained by reaction between the compounds $R_1R_2PCl$ or $R_1R_2PI$, $R_1$ and $R_2$ being the radicals of the general formula (I), with a fluorinated salt, for example CsF. Such a synthesis, in order to prepare the compound $^tBu_2PF$, is, for example, described in the publication Schmutzler et al., *J. Chem. Soc.* (A), 1970, 2359-2364.

According to the invention, the organophosphorus compounds of formula (I) are used in the manufacture of a catalytic system by combination with a metal element in order to form a complex. Overall, the composition of these catalytic systems can be represented by the general formula (II) (this formula does not correspond to the structure of the compounds and complexes present in the catalytic system):

$$M[L_f]_t \qquad (II)$$

in which:
M is a transition metal,
$L_f$ represents at least one organophosphorus ligand of formula (I),
t represents a number between 1 and 10 (limits included).

The metals M which can be complexed are generally all the transition metals of Groups 1b, 2b, 3b, 4b, 5b, 6b, 7b and 8 of the Periodic Table of the Elements, as published in the Handbook of Chemistry and Physics, 51st Edition (1970-1971), by The Chemical Rubber Company.

Mention may more particularly be made, among these metals, of the metals which can be used as catalysts in hydrocyanation reactions. Thus, mention may be made, as nonlimiting examples, of nickel, cobalt, iron, ruthenium, rhodium, palladium, osmium, iridium, platinum, copper, silver, gold, zinc, cadmium or mercury. Nickel is the preferred element for the hydrocyanation of olefins and unsaturated nitriles.

The preparation of the catalytic systems comprising compounds of general formula (I) can be carried out by bringing a solution of a compound of the chosen metal, for example nickel, into contact with a solution of the organophosphorus compound of the invention.

The compound of the metal can be dissolved in a solvent. The metal can occur in the compound employed either at the oxidation state which it will have in the organometallic complex or at a higher oxidation state.

By way of example, it may be indicated that, in the organometallic complexes of the invention, rhodium is at the (I) oxidation state, ruthenium is at the (II) oxidation state, platinum is at the (0) oxidation state, palladium is at the (0) oxidation state, osmium is at the (II) oxidation state, iridium is at the (I) oxidation state and nickel is at the (0) oxidation state.

If, during the preparation of the organometallic complex, the metal is employed at a higher oxidation state, it can be reduced in situ.

Mention may be made, among the compounds of metals M which can be used for the preparation of the organometallic complexes, in particular when the metal is nickel, as nonlimiting examples, of the following nickel compounds:

the compounds in which the nickel is at the zero oxidation state, such as potassium tetracyanonickelate K$_4$[Ni (CN)$_4$], bis(acrylonitrile)nickel(0), bis(1,5-cyclooctadiene)nickel (also known as Ni(cod)$_2$) and the derivatives comprising ligands, such as tetrakis(triphenylphosphine)nickel(0), nickel compounds, such as the carboxylates (in particular the acetate), carbonate, bicarbonate, borate, bromide, chloride, citrate, thiocyanate, cyanide, formate, hydroxide, hydrophosphite, phosphite, phosphate and derivatives, iodide, nitrate, sulfate, sulfite, arylsulfonates and alkylsulfonates.

When the nickel compound used corresponds to an oxidation state of the nickel of greater than 0, a reducing agent for the nickel which preferably reacts with the latter under the conditions of the reaction is added to the reaction medium. This reducing agent can be organic or inorganic. Mention may be made, as nonlimiting examples, of borohydrides, such as NaBH$_4$, KBH$_4$, Zn powder, magnesium or hydrogen.

When the nickel compound used corresponds to the 0 oxidation state of the nickel, it is also possible to add a reducing agent of the type of those mentioned above but this addition is not absolutely essential.

When use is made of an iron compound, the same reducing agents are suitable. In the case of palladium, the reducing agents can in addition be components of the reaction medium (solvent, olefin).

The organic compounds comprising at least one ethylenic double bond more particularly employed in the present process are diolefins, such as butadiene, isoprene, 1,5-hexadiene or 1,5-cyclooctadiene, ethylenically unsaturated aliphatic nitriles, particularly linear pentenenitriles, such as 3-pentenenitrile or 4-pentenenitrile, and also monoolefins, such as styrene, methylstyrene, vinylnaphthalene, cyclohexene or methylcyclohexene, and also the mixtures of several of these compounds.

The pentenenitriles can comprise, in addition to 3-pentenenitrile and 4-pentenenitrile, amounts, generally minor amounts, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile or butadiene, for example originating from the prior hydrocyanation reaction of butadiene to give unsaturated nitriles.

This is because, during the hydrocyanation of butadiene, not insignificant amounts of 2-methyl-3-butenenitrile and 2-methyl-2-butenenitrile are formed with the linear pentenenitriles.

The catalytic system used for the hydrocyanation according to the process of the invention can be prepared before it is introduced into the reaction region, for example by addition, to the compound of formula (I), alone or dissolved in a solvent, of the appropriate amount of compound of the transition metal chosen and optionally of the reducing agent. It is also possible to prepare the catalytic system "in situ" by simple addition of the compound of formula (I) and of the compound of the transition metal to the hydrocyanation reaction medium, before or after the addition of the compound to be hydrocyanated.

The amount of compound of nickel or of another transition metal used is chosen in order to obtain a concentration, as moles of transition metal per mole of organic compounds to be hydrocyanated or isomerized, of between $10^{-4}$ and 1 and preferably between 0.005 and 0.5 mol of nickel or of the other transition metal employed.

The amount of compound of formula (I) used to form the catalyst is chosen so that the number of moles of this compound, with respect to 1 mol of transition metal, is from 0.5 to 100 and preferably from 0.5 to 50.

Although the reaction is generally carried out without solvent, it can be advantageous to add an inert organic solvent. The solvent can be a solvent for the catalyst which is miscible with the phase comprising the compound to be hydrocyanated at the hydrocyanation temperature. Mention may be made, as examples of such solvents, of aromatic, aliphatic or cycloaliphatic hydrocarbons.

The hydrocyanation reaction is generally carried out at a temperature of 10° C. to 200° C. and preferably of 30° C. to 120° C. It can be carried out in a single-phase medium.

The hydrocyanation process of the invention can be carried out continuously or batchwise.

The hydrogen cyanide employed can be prepared from metal cyanides, in particular sodium cyanide, or cyanohydrins, such as acetone cyanohydrin, or by any other known synthetic process, such as the Andrussow process, which consist in reacting methane with ammonia and air.

Water-free hydrogen cyanide is introduced into the reactor in the gaseous form or in the liquid form. It can also be dissolved beforehand in an organic solvent.

In the context of a batchwise use, it is possible in practice to charge, to a reactor purged beforehand using an inert gas (such as nitrogen or argon), either a solution comprising all or a portion of the various constituents, such as the compound of formula (I), the transition metal (nickel) compound, the optional reducing agent and the optional solvent, or said constituents separately. Generally, the reactor is then brought to the chosen temperature and then the compound to be hydrocyanated is introduced. The hydrogen cyanide is then itself introduced, preferably continuously and uniformly.

When the reaction (the evolution of which can be monitored by assaying withdrawn samples) is complete, the reaction mixture is withdrawn after cooling and the reaction products are isolated and separated, for example by distillation.

Advantageously, the synthesis of dinitriles, such as adiponitrile, from diolefins (butadiene) is obtained in two successive stages. The first stage consists in hydrocyanating a double bond of the diolefin in order to obtain an unsaturated mononitrile. The second stage consists in hydrocyanating the unsaturation of the mononitrile in order to obtain the corresponding dinitrile or dinitriles. These two stages are generally carried out with a catalytic system comprising an organometallic complex of the same nature. However, the organophosphorus compound/metal element and concentration of the catalyst ratios can be different. In addition, it is preferable to combine, with the catalytic system, a cocatalyst or promoter in the second stage. This cocatalyst or promoter is generally a Lewis acid.

The Lewis acid used as cocatalyst makes it possible in particular, in the case of the hydrocyanation of ethylenically unsaturated aliphatic nitriles, to improve the linearity of the dinitriles obtained, that is to say the percentage of linear dinitrile with respect to the combined dinitriles formed, and/ or to increase the activity and the life time of the catalyst.

The term "Lewis acid" is understood to mean, in the present text, according to the normal definition, compounds which accept electron pairs.

It is possible in particular to employ the Lewis acids mentioned in the work edited by G. A. Olah, "Friedel-Crafts and Related Reactions", Volume I, pages 191 to 197 (1963).

The Lewis acids which can be employed as cocatalysts in the present process are chosen from the compounds of the elements of Groups Ib, IIb, IIIa, IIIb, IVa, IVb, Va, Vb, VIb, VIIb and VIII of the Periodic Table of the Elements. These compounds are generally salts, in particular halides, such as chlorides or bromides, sulfates, sulfonates, halosulfonates, perhaloalkylsulfonates, in particular fluoroalkylsulfonates or perfluoroalkylsulfonates, carboxylates and phosphates.

Mention may be made, as nonlimiting examples of such Lewis acids, of zinc chloride, zinc bromide, zinc iodide, manganese chloride, manganese bromide, cadmium chloride, cadmium bromide, stannous chloride, stannous bromide, stannous sulfate, stannous tartrate, indium trifluoromethylsulfonate, chlorides or bromides of the rare earth metal elements, such as lanthanum, cerium, praseodymium, neodymium, samarium, europium, gadolinium, terbium, dysprosium, hafnium, erbium, thallium, ytterbium and lutetium, cobalt chloride, ferrous chloride or yttrium chloride.

Use may also be made, as Lewis acid, of organometallic compounds, such as triphenylborane, titanium isopropoxide or the compounds described in French patent applications FR 2 926 816 and FR 2 937 321.

It is possible, of course, to employ mixtures of several Lewis acids, as described, for example, in French patent application FR 2 941 455.

Preference is very particularly given, among Lewis acids, to zinc chloride, zinc bromide, stannous chloride, stannous bromide, triphenylborane and zinc chloride/stannous chloride mixtures.

The Lewis acid cocatalyst employed generally represents from 0.01 to 50 mol per mole of transition metal compound, more particularly of nickel compound, and preferably from 1 to 10 mol per mole.

The unsaturated mononitriles employed in this second stage are advantageously linear pentenenitriles, such as 3-pentenenitrile, 4-pentenenitrile and their mixtures.

These pentenenitriles can comprise amounts, generally minor amounts, of other compounds, such as 2-methyl-3-butenenitrile, 2-methyl-2-butenenitrile or 2-pentenenitrile.

The catalytic solution used for the hydrocyanation in the presence of Lewis acid can be prepared before it is introduced into the reaction region, for example by addition, to the compound of formula (I), of the appropriate amount of compound of the transition metal chosen, of Lewis acid and optionally of the reducing agent. It is also possible to prepare the catalytic solution "in situ" by simple addition of these various constituents to the reaction medium.

It is also possible, under the conditions of the hydrocyanation process of the present invention, and in particular by carrying out the operation in the presence of the catalytic system described above comprising a compound of formula (I) and at least one compound of a transition metal, to bring about, in the absence of hydrogen cyanide, the isomerization of 2-methyl-3-butenenitrile to give pentenenitriles and more generally of unsaturated branched nitriles to give unsaturated linear nitriles.

The 2-methyl-3-butenenitrile subjected to the isomerization according to the invention can be employed alone or as a mixture with other compounds. Thus, it is possible to use 2-methyl-3-butenenitrile as a mixture with 2-methyl-2-butenenitrile, 4-pentenenitrile, 3-pentenenitrile, 2-pentenenitrile, butadiene.

It is particularly advantageous to treat the reaction mixture originating from the hydrocyanation of butadiene by HCN in the presence of at least one compound of formula (I) and of at least one compound of a transition metal, more preferably of a compound of nickel in the 0 oxidation state, as defined above. In the context of this preferred alternative form, as the catalytic system is already present for the reaction for the hydrocyanation of butadiene, it is sufficient to halt any introduction of hydrogen cyanide in order to allow the isomerization reaction to take place.

It is possible, if appropriate, in this alternative form, to carry out a gentle flushing of the reactor using an inert gas, such as nitrogen or argon, for example, in order to drive off the hydrocyanic acid which might still be present.

The isomerization reaction is generally carried out at a temperature between 10° C. and 200° C. and preferably between 60° C. and 140° C.

In the preferred case of an isomerization immediately following the reaction for the hydrocyanation of butadiene, it will be advantageous to operate at the temperature at which the hydrocyanation was carried out or slightly above.

As for the process for the hydrocyanation of ethylenically unsaturated compounds, the catalytic system used for the isomerization can be prepared before it is introduced into the reaction region, for example by mixing the compound of formula (I), the appropriate amount of compound of the transition metal chosen and optionally the reducing agent. It is also possible to prepare the catalytic system "in situ" by simple addition of these various constituents to the reaction medium. The amount of compound of the transition metal and more particularly of nickel used and also the amount of compound of formula (I) are the same as for the hydrocyanation reaction.

Although the isomerization reaction is generally carried out without solvent, it can be advantageous to add an inert organic solvent which can be used as extraction solvent subsequently. This is in particular the case when such a solvent has been employed in the reaction for the hydrocyanation of butadiene which was used to prepare the medium subjected to the isomerization reaction. Such solvents can be chosen from those which were mentioned above for the hydrocyanation.

However, the preparation of dinitrile compounds by hydrocyanation of an olefin, such as butadiene, can be carried out using a catalytic system in accordance with the invention for the stages of formation of the unsaturated nitriles and the isomerization stage above, it being possible for the reaction for the hydrocyanation of the unsaturated nitriles to give dinitriles to be carried out with a catalytic system in accordance with the invention or any other catalytic system already known for this reaction.

Likewise, the reaction for the hydrocyanation of the olefin to give unsaturated nitriles and the isomerization of the latter can be carried out with a catalytic system different from that of the invention, the stage of hydrocyanation of the unsaturated nitriles to give dinitriles being carried out with a catalytic system in accordance with the invention.

Other details and advantages of the invention will be illustrated by the examples given below solely by way of indication, without a limiting nature.

EXAMPLES

Abbreviations Used
  Cod: cyclooctadiene
  $Ni(Cod)_2$: bis(1,5-cyclooctadiene)nickel
  3PN: 3-pentenenitrile
  AdN: Adiponitrile
  ESN: ethylsuccinonitrile
  MGN: methylglutaronitrile
  DN: dinitrile compounds (AdN, MGN or ESN)
  TIBAO: tetraisobutyldialuminoxane
  TY (DN): true yield of dinitriles, corresponding to the ratio of the number of moles of dinitriles formed to the number of moles of 3PN charged
  Linearity (L): ratio of the number of moles of AdN formed to the number of moles of dinitriles formed (sum of the moles of AdN, ESN and MGN)

The following compounds: 3PN, Ni(Cod)$_2$, ZnCl$_2$, TIBAO and Ph$_2$BOBPh$_2$ (diphenylborinic anhydride), are available commercially.

Example 1

Preparation of the Ligand $^t$Bu$_2$PF

Ligand

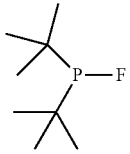

The synthesis of $^t$Bu$_2$PF was published by Schmutzler et al., *J. Chem. Soc.* (A), 1970, 2359-2364.

Liquid $^t$Bu$_2$PCl (2.20 g, 27.3 mmol) is slowly added (15 min) to a suspension of CsF (4.63 g, 89.2 mmol) in MeCN (10 cm$^3$) and the mixture is stirred at ambient temperature for 2 h. The reaction mixture is subsequently filtered and the colorless solution obtained is separated by fractional distillation. The first fraction comprises only acetonitrile, while the second fraction (boiling point 110-112° C.) and the third fraction (129-131° C.) are similar according to the $^{31}$P and $^1$H NMR analyses and were combined (total volume 13.5 cm$^3$). They comprise only acetonitrile and $^t$Bu$_2$PF $^{31}$P{$^1$H} NMR (in situ): 216.1 (d, J$_{PF}$=862 Hz), $^1$H NMR (CDCl$_3$) 1.95 (3H, s, MeCN), 1.12 (6H, dd, J$_{HP}$=11.50 Hz, J$_{HF}$=1.65 Hz) The $^t$Bu$_2$PF:MeCN molar ratio is 1:45 in the solution

Examples 2 to 4

Hydrocyanation of 3-PN to give AdN

The general procedure used is as follows.

The following are successively charged, under an argon atmosphere, to a 60 ml glass tube of Schott type equipped with a septum stopper:
  the ligand (1 mmol, 2 equivalents of P)
  1.24 g (15 mmol, 30 equivalents) of anhydrous 3PN
  138 mg (0.5 mmol, 1 equivalent) of Ni(cod)$_2$
  Lewis acid (see table 1 for the nature and the amount)

The mixture is brought with stirring to 70° C. Acetone cyanohydrin is injected into the reaction medium via a syringe driver at a flow rate of 0.45 ml per hour. After injecting for 3 hours, the syringe driver is halted. The mixture is cooled to ambient temperature, diluted with acetone and analyzed by gas chromatography.

The results are combined in the following table:

TABLE

| Example | Ligand | Lewis acid | Lewis acid/Ni (molar) | Linearity | TY (DN) |
|---|---|---|---|---|---|
| 2 | $^t$Bu$_2$PF | ZnCl$_2$ | 1 | 50 | 4.3 |
| 3 | $^t$Bu$_2$PF | TIBAO | 0.5 | 46.8 | 10 |
| 4 | $^t$Bu$_2$PF | Ph$_2$BOBPh$_2$ | 0.5 | 52.1 | 6 |

The invention claimed is:

1. A process for the hydrocyanation of an organic compound having at least one ethylenic unsaturation, comprising: reacting, in a liquid medium, the organic compound with hydrogen cyanide in the presence of a catalyst comprising a metal element chosen from transition metals and an organophosphorus ligand that comprises a compound corresponding to the general formula (I):

in which:
  each of R$_1$ and R$_2$, which are identical or different, represents:
  a linear or branched alkyl radical having from 1 to 12 carbon atoms which can comprise heteroatoms, or a radical comprising a substituted or unsubstituted aromatic or cycloaliphatic radical which can comprise heteroatoms, and the respective covalent bonds between P and R$_1$, and between P and R$_2$ are each P—C bonds.

2. The process as claimed in claim 1, wherein R$_1$ and R$_2$ represent a linear or branched alkyl radical having from 1 to 12 carbon atoms which can comprise heteroatoms.

3. The process as claimed in claim 1 or 2, wherein the compound of formula (I) is $^t$Bu$_2$PF.

4. The process as claimed in claim 1, wherein the metal element is selected from the group consisting of nickel, cobalt, iron, ruthenium, rhodium, palladium, osmium, iridium, platinum, copper, silver, gold, zinc, cadmium and mercury.

5. The process as claimed in claim 1, wherein the catalyst is expressed by the general formula (II):

$$M[L_f]_t \qquad (II)$$

wherein:
  M is a transition metal,
  L$_f$ represents at least one organophosphorus ligand of formula (I), and
  t represents a number between 1 and 10 (limits included).

6. The process as claimed in claim 1, wherein the organic compound comprising at least one ethylenic unsaturation is chosen from diolefins, ethylenically unsaturated aliphatic nitriles, monoolefins, and the mixtures of several of these compounds.

7. The process of claim 6, wherein the organic compound having at least one ethylenic unsaturation is chosen from butadiene, isoprene, 1,5-hexadiene 1,5-cyclooctadiene, 3-pentenenitrile, 4-pentenenitrile, styrene, methylstyrene, vinylnaphthalene, cyclohexene methylcyclohexene, and a mixture thereof.

8. The process as claimed in claim 1, wherein the amount of the transition metal is chosen so that there is, per mole of the organic compound to be hydrocyanated, between 10$^{-4}$ and 1 mole of the transition metal employed and the amount of the organophosphorus compound used is chosen so that the number of moles of the organophosphorus compound, with respect to 1 mole of the transition metal, is from 0.5 to 100.

9. The process as claimed in claim 8, wherein the transition metal is nickel.

10. The process as claimed in claim 1, wherein it is a process of hydrocyanation to give dinitriles, that the ethylenically unsaturated compounds are ethylenically unsaturated nitrile compounds and that the operation is carried out in the presence of a catalyst comprising at least one compound of a transition metal, at least one compound of formula (I) and a cocatalyst consisting of at least one Lewis acid.

11. The process as claimed in claim 10, wherein the ethylenically unsaturated nitrile compounds are chosen from linear pentenenitriles.

12. The process as claimed in claim 11, wherein the linear pentenenitriles are chosen from 3-pentenenitrile, 4-pentenenitrile, and their mixtures.

13. The process as claimed in claim 10, wherein the Lewis acid employed as cocatalyst is chosen from compounds of the elements of Groups Ib, IIb, IIIa, IIIb, IVa, IVb, Va, Vb, VIb, VIIb and VIII of the Periodic Table of the Elements.

14. The process as claimed in claim 10, wherein the Lewis acid is chosen from zinc chloride, zinc bromide, zinc iodide, manganese chloride, manganese bromide, cadmium chloride, cadmium bromide, stannous chloride, stannous bromide, stannous sulfate, stannous tartrate, indium trifluoromethylsulfonate, chlorides or bromides of the rare earth metal elements, cobalt chloride, ferrous chloride, yttrium chloride and their mixtures, or organometallic compounds.

15. The process as claimed in claim 1, wherein the organic compound is butadiene and the hydrocyanation product of butadiene is isomerized in the absence of hydrogen cyanide, in the-presence of a catalyst comprising at least one compound of formula (I) and at least one compound of a transition metal.

16. A hydrocyanation process, comprising reacting, in a liquid medium, an organic compound chosen from ethylenically unsaturated aliphatic nitriles and mixtures thereof with hydrogen cyanide in the presence of:

a catalyst according to formula (II):

$$M[L_f]_t \qquad (II)$$

wherein:
M is a transition metal,
$L_f$ is $^tBu_2PF$, and
t is a number of from 1 to 10, and
a cocatalyst consisting of at least one Lewis acid.

17. The process as claimed in claim 16, wherein the transition metal is nickel.

* * * * *